US007966890B2

(12) United States Patent
Dingmann et al.

(10) Patent No.: US 7,966,890 B2
(45) Date of Patent: Jun. 28, 2011

(54) HIGH FREQUENCY MULTI-AXIS SIMULATION SYSTEM

(75) Inventors: David Louis Dingmann, St. Paul, MN (US); Eric Thomas Gagner, Minnetonka, MN (US); Troy D. Nickel, Minnetonka, MN (US); Steven R. Seeman, Stillwater, MN (US); Andrew D. White, Minneapolis, MN (US)

(73) Assignee: Bose Corporation, Framingham, MA (US)

( * ) Notice: Subject to any disclaimer, the term of this patent is extended or adjusted under 35 U.S.C. 154(b) by 595 days.

(21) Appl. No.: 12/146,094

(22) Filed: Jun. 25, 2008

(65) Prior Publication Data

US 2009/0326889 A1    Dec. 31, 2009

(51) Int. Cl.
*G05B 15/02* (2006.01)
*G05B 11/01* (2006.01)
(52) U.S. Cl. .............. 73/849; 73/856; 700/9; 702/43
(58) Field of Classification Search ............ 700/9, 19; 73/849, 856; 702/43, 75; 703/2, 4
See application file for complete search history.

(56) References Cited

U.S. PATENT DOCUMENTS

| | | | | |
|---|---|---|---|---|
| 3,797,304 A | * | 3/1974 | Klinger | 73/794 |
| 4,056,974 A | | 11/1977 | Klinger et al. | |
| 4,181,029 A | | 1/1980 | Talbott, Jr. | |
| 4,802,365 A | * | 2/1989 | Sallberg et al. | 73/808 |
| 5,670,708 A | | 9/1997 | Vilendrer | |
| 6,058,784 A | * | 5/2000 | Carroll et al. | 73/856 |
| 7,024,323 B2 | * | 4/2006 | Porter et al. | 702/77 |
| 7,546,775 B2 | * | 6/2009 | Chinavare | 73/849 |
| 7,624,648 B2 | * | 12/2009 | Nickel et al. | 73/856 |
| 7,913,573 B2 | * | 3/2011 | Schulz et al. | 73/856 |
| 2002/0017144 A1 | | 2/2002 | Miles et al. | |
| 2002/0162400 A1 | * | 11/2002 | Xie et al. | 73/812 |
| 2004/0016301 A1 | | 1/2004 | Moreno et al. | |
| 2006/0174709 A1 | | 8/2006 | Hobbs | |
| 2007/0068274 A1 | | 3/2007 | Olson et al. | |
| 2008/0295606 A1 | * | 12/2008 | Chinavare | 73/849 |
| 2009/0000388 A1 | * | 1/2009 | Nickel et al. | 73/856 |
| 2009/0326837 A1 | * | 12/2009 | White | 702/43 |

FOREIGN PATENT DOCUMENTS

WO          9914749          3/1999

OTHER PUBLICATIONS

"Adaptive Neural Network Travking Control of MIMO Nonlinear Systems with Unknown Dead Zones and Control Directions", Zhang et al, IEEE Transactions on Neural Networks, vol. 20, No. 3, Mar. 2009.*
"On-line Actuator State Monitoring of a MIMO Bioprocess", Deng et al, Department of Systems Engineering, Okayama University, Asian Control Conference, Jul. 2004.*

(Continued)

*Primary Examiner* — Michael D Masinick

(57) ABSTRACT

A multi-axis fatigue testing device includes a multi-axis test fixture having a multiple input, multiple output mechanical linkage driven by a plurality of actuators and a controller operating each of the plurality of actuators in real time and in synchronization to produce user-defined multiple fatigue cycle profiles. At least one of the actuators driving the mechanical linkage acts against an artificial load characterized by a stiffness. The stiffness is selected to increase a resonance frequency of the test fixture to allow fatigue testing at higher frequencies for a wider range of samples.

14 Claims, 6 Drawing Sheets

OTHER PUBLICATIONS

"Evolutionary Design of Interpretable Fuzzy Controllers", Hapke et al, Foundations of Computing and Decision Sciences, 2008.*
International Search Report and Written Opinion dated Mar. 25, 2009 for PCT/US2008/083721.

Sanders, Joan E. et al: "A Bidirectional Load Applicator for the Investigation of Skin Response to Mechanical Stress", IEEE Transactions on Biomedical Engineering, IEEE Service Center, Piscataway, NJ, US, vol. 44, No. 4, Apr. 1, 1997 pp. 290-293.

* cited by examiner

US 7,966,890 B2

HIGH FREQUENCY MULTI-AXIS SIMULATION SYSTEM

BACKGROUND

This disclosure relates to testing devices and methods for medical implant devices.

SUMMARY

A multi-axis fatigue testing device includes a multi-axis test fixture having a multiple input, multiple output mechanical linkage driven by a plurality of actuators and a controller operating each of the plurality of actuators in real time and in synchronization to produce user-defined multiple fatigue cycle profiles. At least one of the actuators driving the mechanical linkage acts against an artificial load characterized by a stiffness. The stiffness is selected to increase a resonance frequency of the test fixture to allow fatigue testing at higher frequencies for a wider range of samples.

One embodiment of the present invention is directed to a high frequency multi-axis simulation system comprising: a test fixture having a MIMO linkage, the MIMO linkage driven by a first actuator and a second actuator, the MIMO linkage acting on a sample to provide simulation along a first simulation axis and a second simulation axis; a controller configured to operate the first and second actuators according to a user-specified first simulation profile and a second-simulation profile; a first artificial load driven by the first actuator; a second artificial load driven by the second actuator; the first and second artificial load increasing a resonant frequency of the simulation system. In an aspect, the first simulation axis is an axial strain and the second simulation axis is a bend angle. In an aspect, a first torsion assembly connected to a first end of a sample holder supporting the sample and a second torsion assembly connected to a second end of the sample holder, the first and second torsion assemblies driven by a third actuator according to a user-specified third simulation profile. In an aspect, the third actuator is operated simultaneously by the controller independently of the first and second actuators. In an aspect, a flow path providing a fluid flow through the sample according to a user-specified fourth simulation profile. In an aspect, the flow path includes a pump providing pulsatile flow through the sample. In an aspect, the first artificial load is a spring. In an aspect, a value of a spring constant characterizing the spring is selected to increase a resonant frequency characterizing the simulation system. In an aspect, the first artificial load further comprises a damper. In an aspect, the resonant frequency characterizing the simulation system is greater than about 5 Hz. In an aspect, the resonant frequency characterizing the simulation system is greater than about 8 Hz. In an aspect, the spring is characterized by a stiffness having a value that is at least ten times greater than a stiffness value characterizing the sample. In an aspect, the user-specified first simulation profile is characterized by a profile frequency, the profile frequency in a frequency range of 4-10 Hz. In an aspect, the user-specified first simulation profile is characterized by a profile frequency, the profile frequency in a frequency range of 12-30 Hz. In an aspect, the first artificial load is an actuator.

Another embodiment of the present invention is directed to a method of eliminating controller tuning by a user, the controller operating a MIMO linkage driven by a first actuator and a second actuator, MIMO linkage acting on a sample characterized by a sample stiffness to provide simulation along a first simulation axis and a second simulation axis, the method comprising applying a first artificial load to the first actuator and a second artificial load to the second actuator wherein the first artificial load is selected to increase a stiffness of the first actuator to a value that is at least ten times larger than the sample stiffness and the second artificial load is selected to increase a stiffness of the second actuator to a value that is at least ten time large than the sample stiffness.

Another embodiment of the present invention is directed to a high frequency multi-axis simulation system comprising: a test fixture having a MIMO linkage, the MIMO linkage driven by a first actuator and a second actuator, the MIMO linkage acting on a sample to provide simulation along at least a first simulation axis and a second simulation axis; a controller configured to operate the first and second actuators according to a user-specified first simulation profile and a second-simulation profile; a first artificial load driven by the first actuator; a second artificial load driven by the second actuator; the first and second artificial load increasing a resonant frequency of the simulation system. In an aspect, the first simulation axis is an axial strain and the second simulation axis is a bend angle. In an aspect, a first torsion assembly connected to a first end of a sample holder supporting the sample and a second torsion assembly connected to a second end of the sample holder, the first and second torsion assemblies driven by a third actuator according to a user-specified third simulation profile. In an aspect, the third actuator is operated simultaneously by the controller independently of the first and second actuators.

DETAILED DESCRIPTION

Figure 1:
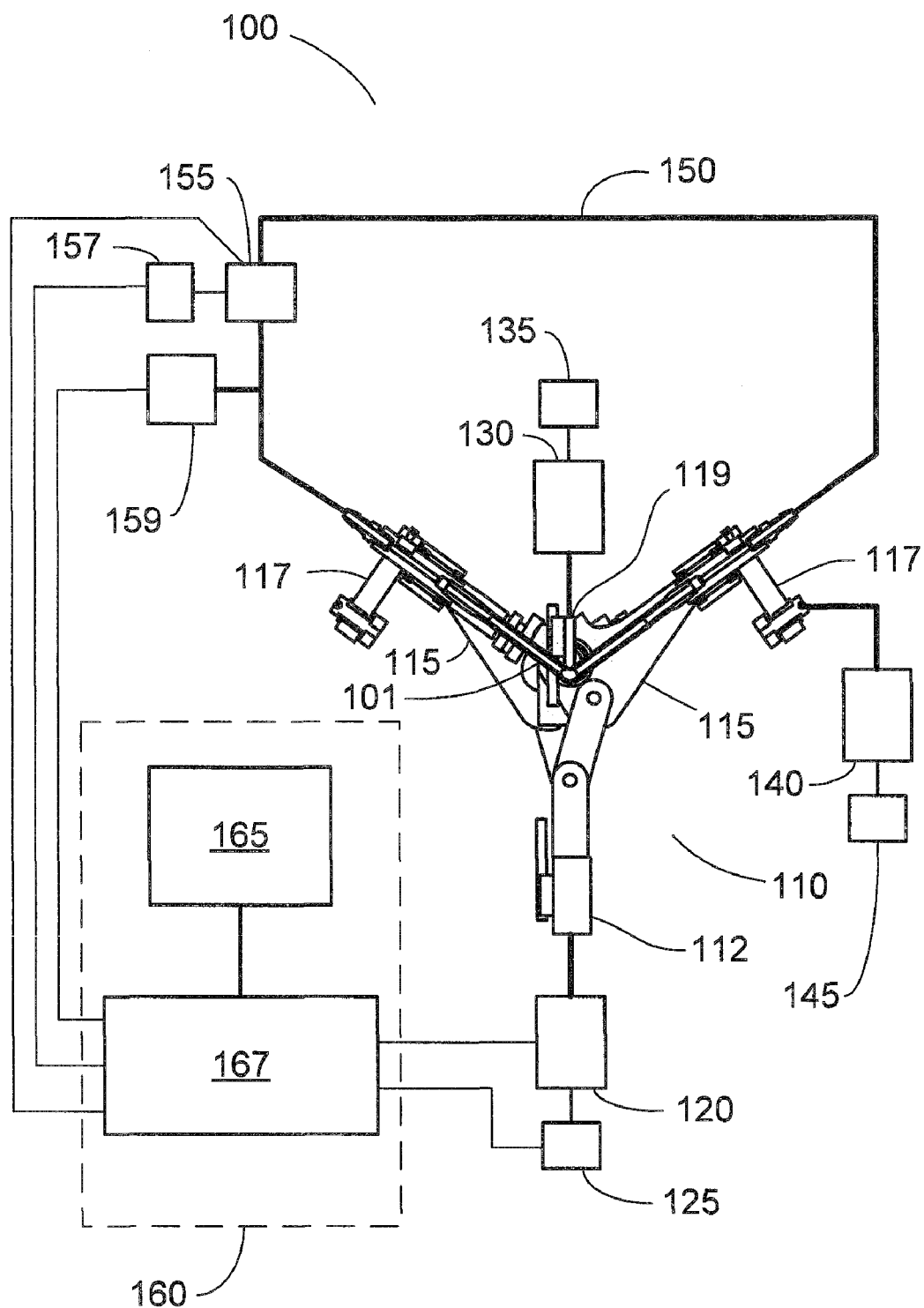
FIG. 1 is a schematic diagram illustrating an embodiment of a multi-axis simulation system.

FIG. 1 is a schematic diagram illustrating an example of a multi-axis simulation system 100. In FIG. 1, a sample is held in a sample holder 101 that is attached to a multi-axis test fixture 110. The sample is preferably an implantable stent but other implantable devices or bioprosthesis devices may be tested with the simulation system 100 shown in FIG. 1.

Test fixture 110 includes a pair of lever arms 115 that are rotatable around a common pivot point. Each lever arm 115 is mechanically linked to a common drive link 112 that is connected to a drive shaft of a first actuator 120, herein referred to as a scissors actuator. As the common drive link 112 is displaced upward in FIG. 1, the lever arms 115 rotate downward around the common pivot point thereby increasing a bend angle of the sample holder 101. As the common drive link 112 is displaced downward in FIG. 1, the lever arms 115 rotate upward toward each other and decreases the bend angle of the sample holder 101. The bend angle of the sample holder is the angle formed by the sample holder ends and a contact point where a bend tool 119 contacts the sample holder 101.

The bend tool 119 contacts the sample holder 101 about midway along the length of the sample holder 101. As the bend tool 119 is displaced downward in FIG. 1, the bend tool 119 axially strains the sample while also bending the sample held in the sample holder 101. The bend tool 119 is driven by a second actuator 130, herein referred to as an extensor actuator. The bend tool may have a curved surface that contacts the sample holder. Other examples of bend tools that may be used are described in U.S. application Ser. No. 11/757,772 filed Jun. 4, 2007, now U.S. Pat. No. 7,546,775, herein incorporated by reference in its entirety.

Each lever arm 115 supports a torsion assembly 117. Each torsion assembly 117 supports an end of the sample holder 101 and is configured to provide a flow path 150 to the sample holder 101 and apply a rotation around a longitudinal axis of the sample holder 101. Rotation of the sample holder 101 is driven by a third actuator 140, herein referred to as a torsion actuator. In a preferred embodiment, a mechanical linkage may be coupled to the torsion actuator 140 and to each torsion assembly 117 such that each end of the sample holder 101 is rotated in an opposite direction when driven by the torsion actuator 140.

Flow path 150 directs a fluid through the sample and sample holder 101. A fourth actuator 155, herein referred to as a pump, moves the fluid around the flow path and is monitored by a pump sensor 157. In a preferred embodiment, pump 155 provides a pulsatile flow through the flow path 150. Examples of pulsatile flow system are disclosed in U.S. Pat. No. 5,670,708 issued on Sep. 23, 1997 and is incorporated herein by reference in its entirety. It is believed that a pulsatile flow through the sample causes a hoop strain in the sample that more closely simulates an in-use condition of the sample in, for example, an artery. A flow path sensor 159 monitors one or more conditions of the fluid in the flow path. Examples of flow path sensors include, without being limiting, pressure sensors, mass or volume flow sensors, pH sensors, particle sensors, temperature sensors, and chemical sensors. The fluid may be a saline mixture that simulates the expected characteristics of a fluid contacting the sample during use. The fluid may include nutrient media that can support live cells if the sample contains living cells.

The view shown in FIG. 1 shows only one sample but the multi-axis test fixture 110 is preferably configured to support more than one sample and more preferably support at least 10 samples simultaneously. Each sample may be connected to a separate flow path or groups of samples may share a flow path.

A controller 160 manages the operation of the simulation system 100 and includes a computer 165 and an interface module 167. The computer 165 includes I/O devices such as a display for viewing information and input devices such as a keyboard, mouse, touch pad, or other similar devices for entering information into the computer. The computer 165 includes a processor that executes a control program and computer-readable medium that stores the control program and data received from a user or sensors 125, 135, 145, 157, 159. Interface module 167 receives commands from the computer and operates each of the actuators 120, 130, 140, 155 in response to the received commands and to data from sensors 125, 135, 145, 157, 159. For the purposes of clarity, FIG. 1 does not show all the control lines between the interface module 167 and each sensor and actuator.

The control program enables a user to select or set various parameters that define the operation of the multi-axis simulator. An example of such a control program is the WinTest® PCI Controls program available from the ElectroForce Systems Group of Bose Corporation of Eden Prairie, Minn. For example and without being limiting, if a user wants to perform a fatigue test on the sample, the user may enter the number of fatigue cycles to perform and cycle profiles for each of the desired simulation axes. Each cycle profile may be designed independently of the other cycle profiles. For example, the user may select a square wave profile from a list of predetermined cycle profiles for the pulsatile pump and enter the desired cycle frequency and the maximum and minimum values for the desired pump pressure. The user may select a sine wave profile for the torsion applied to the sample and enter the desired torsion cycle frequency and the maximum and minimum values for the desired torsion profile. The user may enter a user-defined bend profile as X-Y data pairs and a different user-defined axial strain profile. The control program stores the entered data and periodically sends commands to the interface module to control the operation of the test. The control program receives sensor information from the interface module and stores the sensor information for later analysis.

In the configuration shown in FIG. 1, the sample experiences simultaneous simulation along four axes; hoop strain, torsion, axial strain and bend angle. It is believed that multi-axis simulation provides a more realistic simulation of expected in-use conditions and provides more reliable information relative to information from a simple bend fatigue test. The sample hoop strain is dominated by the pulsatile flow profile and can be run independently of the other simulation axes without significant error. Similarly, the sample torsion is dominated by the axial rotation controlled by the torsion actuator 140 following the user-input torsion profile and can also be run independently of the other simulation axes without significant error. The sample axial strain and bend angle, however, result from a combination of displacements from the scissors actuator 120 and the extensor actuator 130 due to the mechanical linkages of the test fixture 110. The linkage between the axial strain and bend angle simulation axes is sufficiently strong such that a sinusoidal profile applied to both the scissors actuator and extensor actuator can result in a non-sinusoidal sample axial strain and bend angle. Furthermore, the maximum sample axial strain or bend angle may be greater than the desired maximum when the linkage between the axial strain and bend angle simulation axes is not taken into account. The test fixture 110 shown in FIG. 1 is an example of a multiple-input-multiple-output (MIMO) linkage. In the example of FIG. 1, the multiple inputs are the displacements, also referred to as the position, of the scissors actuator and extensor actuator and the multiple outputs are the sample axial strain and sample bend angle. Although the user can specify the axial strain independently of the bend angle, the scissors actuator should not be operated independently from the extensor actuator because the movement of either of the scissors actuator or the extensor actuator can affect the axial strain and bend angle of the sample. U.S. application Ser. No. 11/768,675 filed Jun. 26, 2007, now U.S. Pat. No. 7,624,648, describes methods for controlling MIMO linkages and is incorporated herein by reference in its entirety.

Figure 2:
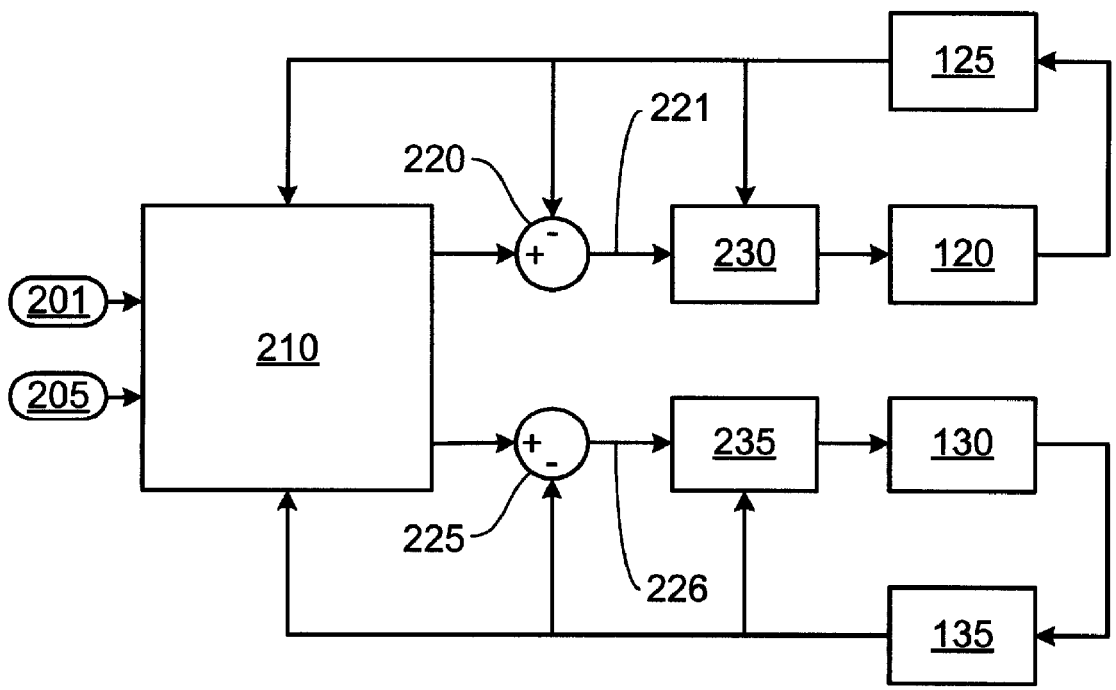
FIG. 2 is a block diagram of a portion of a controller for the system shown in FIG. 1.

FIG. 2 is a block diagram of a portion of a controller for the system shown in FIG. 1 where the same reference number refers to the same structure. In FIG. 2, user-defined cycle profiles for sample axial strain 201 and sample bend angle 205 are sent to a waveform sequence generator 210. The waveform sequence generator 210 converts the user-defined strain and bend angle values to actuator displacements based on a geometric model of the test fixture stored in the computer. Each actuator 120, 130 is controlled by a feedback controller 230, 235, respectively. Sensors 125 and 135 monitor a position of the drive shaft of actuators 120 and 130, respectively. Actuators 120 and 130 are preferably moving magnet linear motors although other embodiments may use other types of actuators to operate the test fixture. Sensors 125 and 135 are preferably LVDT position sensors although other embodiments may use other types of sensors available in the sensor art. A summing module 220, 225 generates an error signal 221, 226 representing a difference between the actuator displacement from the waveform sequence generator 210 and the sensed displacement from sensors 125, 135. Error signals 221 and 226 are input to their respective feedback controllers 230 and 235.

Figure 3:
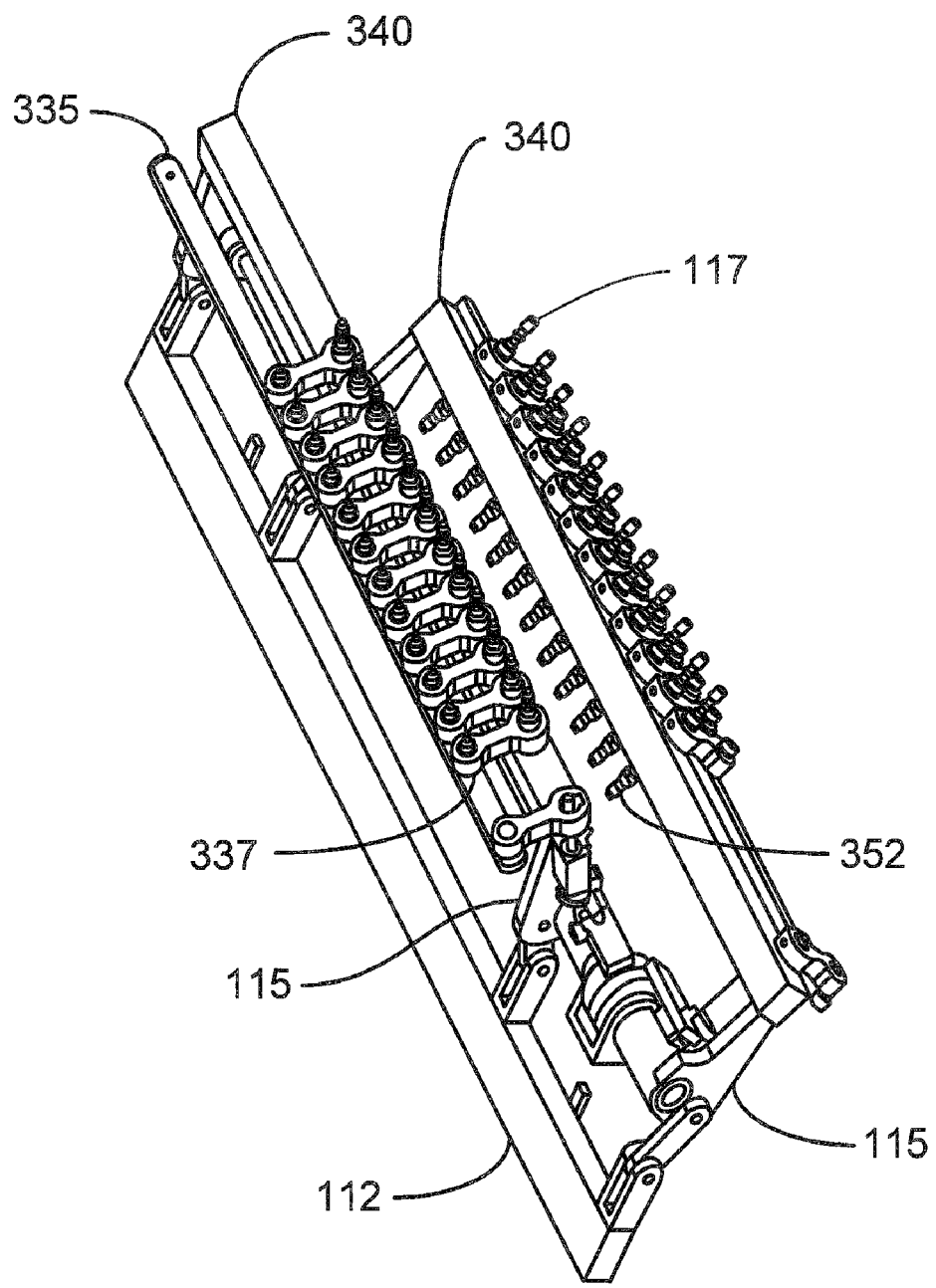
FIG. 3 is a perspective view of the test fixture shown in FIG. 1.

FIG. 3 is a perspective view of the test fixture shown in FIG. 1 and illustrates an example where more than one stent may be tested simultaneously thereby reducing overall testing time while increasing statistical confidence of the results. For purposes of clarity, the bend tool assembly and sample holder are not shown in FIG. 3 and the same reference numbers refer to the same structures as in FIG. 1. In the example shown in FIG. 3, a barb-type grip 352 is used to hold the sample holder but other types of grips may be used according to the sample being tested.

In FIG. 3, torsion assemblies 117 are supported by a bar 340 attached to lever arm 115. One end of a torsion lever arm 337 is pivotally attached to the torsion assembly 117 and the other end of the torsion lever arm 337 is pivotally attached to a torsion linkage 335. The torsion linkage 335 is mechanically linked to an actuator, not shown. As the torsion linkage 335 is displaced, the torsion lever arm 337 applies a rotation to each torsion assembly on the support bar 340. Each torsion linkage 335 may be operated independently by a separate actuator. In a preferred embodiment, a single actuator drives both torsion linkages 335 such that torsion assemblies on one support bar are rotated in an opposite direction to the rotation of the torsion assemblies on the other support bar.

Figure 4:
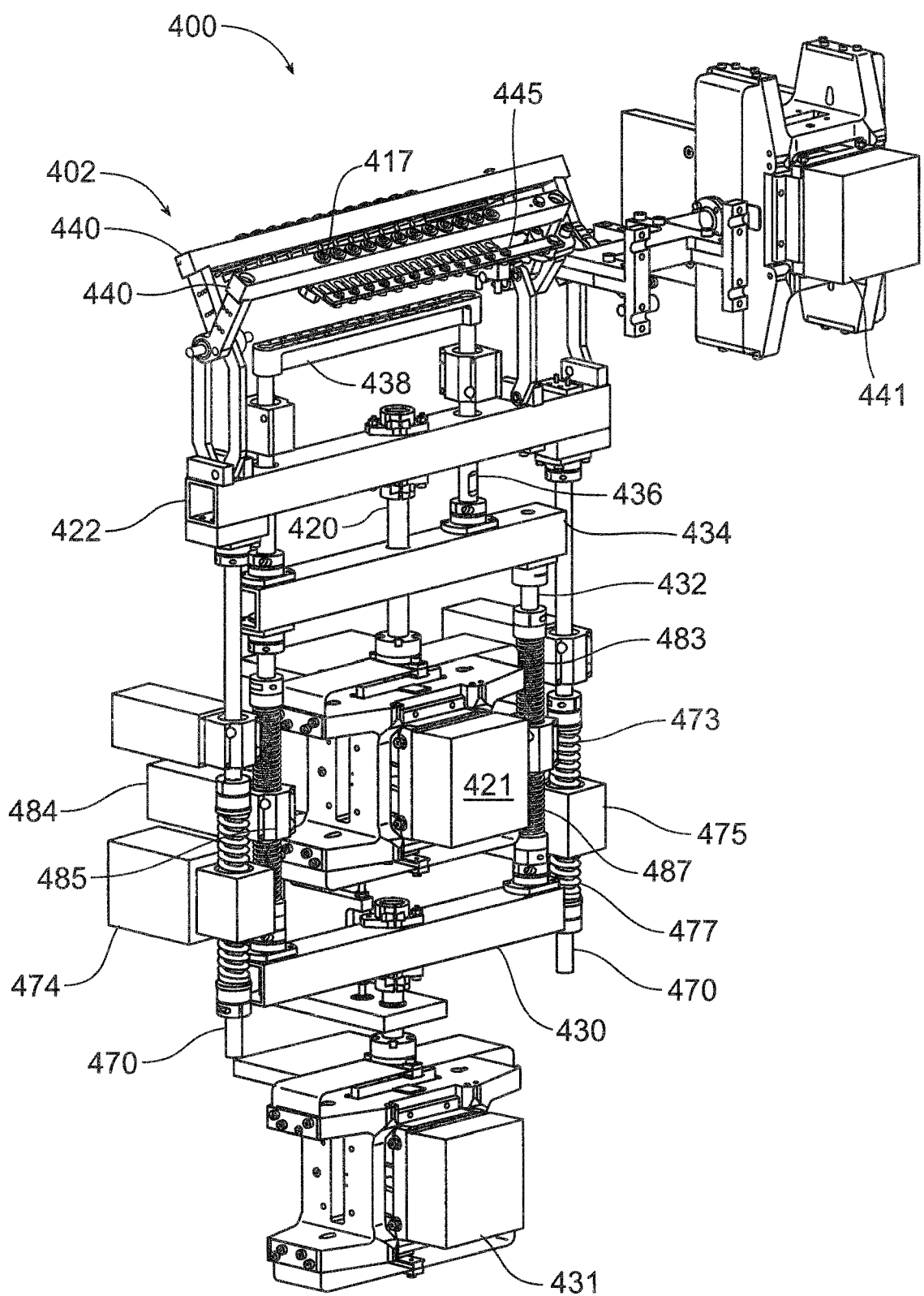
FIG. 4 is a perspective view of a test frame in another embodiment of a multi-axis simulation system.

FIG. 4 is a perspective view of a test frame 400 of another embodiment of a multi-axis simulation system. In FIG. 4, an actuator 431, herein referred to as an extensor actuator, is mechanically linked to lower crossbar 430, bypass rods 432, upper crossbar 434, upper rods 436, and mezzanine crossbar 438. A bend tool assembly, not shown, is mechanically linked to the mezzanine crossbar 438 and contacts a sample holder, not shown, from above the sample holder relative to the orientation shown in FIG. 4. Different bend tool assemblies may be used depending on the type of samples tested. In the orientation shown in FIG. 4, as the extensor actuator 431 moves the lower crossbar 430 in a downward direction, the bend tool assembly contacts the sample holder and imparts an axial strain on the sample and also reduces the bend angle of the sample. As the extensor actuator 431 moves the lower crossbar 430 in an upward direction, the bend tool increases the bend angle of the sample and reduces the axial stain imparted to the sample.

Actuator 421, herein referred to as a scissors actuator, is mechanically linked to support rod 420 and scissors crossbar 422. Support rod 420 freely passes through an opening in the upper crossbar 434 such that the support rod 420 does not contact the upper crossbar 434. The scissors crossbar 422 is mechanically linked to the scissors test fixture 402 and operates the lever arms supporting torsion assembly bar 440. In the orientation shown in FIG. 4, as the scissors actuator 421 moves the support rod 420 in a downward direction, the lever arms of the scissors text fixture are rotated in a downward direction causing the sample bend angle to increase. As the scissors actuator 421 moves the support rod 420 in an upward direction, the lever arms of the scissors text fixture are rotated in an upward direction causing the sample bend angle to decrease.

Actuator 441, herein referred to as a torsion actuator, is mechanically linked to torsion lever arm 445. The torsion lever arm 445 is mechanically linked to each of the torsion assemblies 417 supported by a torsion assembly support 440. In the orientation shown in FIG. 4, as the torsion actuator 441 moves the torsion lever arm 445 to the left, the torsion lever arm 445 applies a clockwise rotation when viewing along the torsion assembly 417 from the top. A second torsion lever arm is hidden in the view of FIG. 4 but is configured to apply a clockwise rotation to the sample when viewing along the second torsion assembly from the top.

Figure 5:
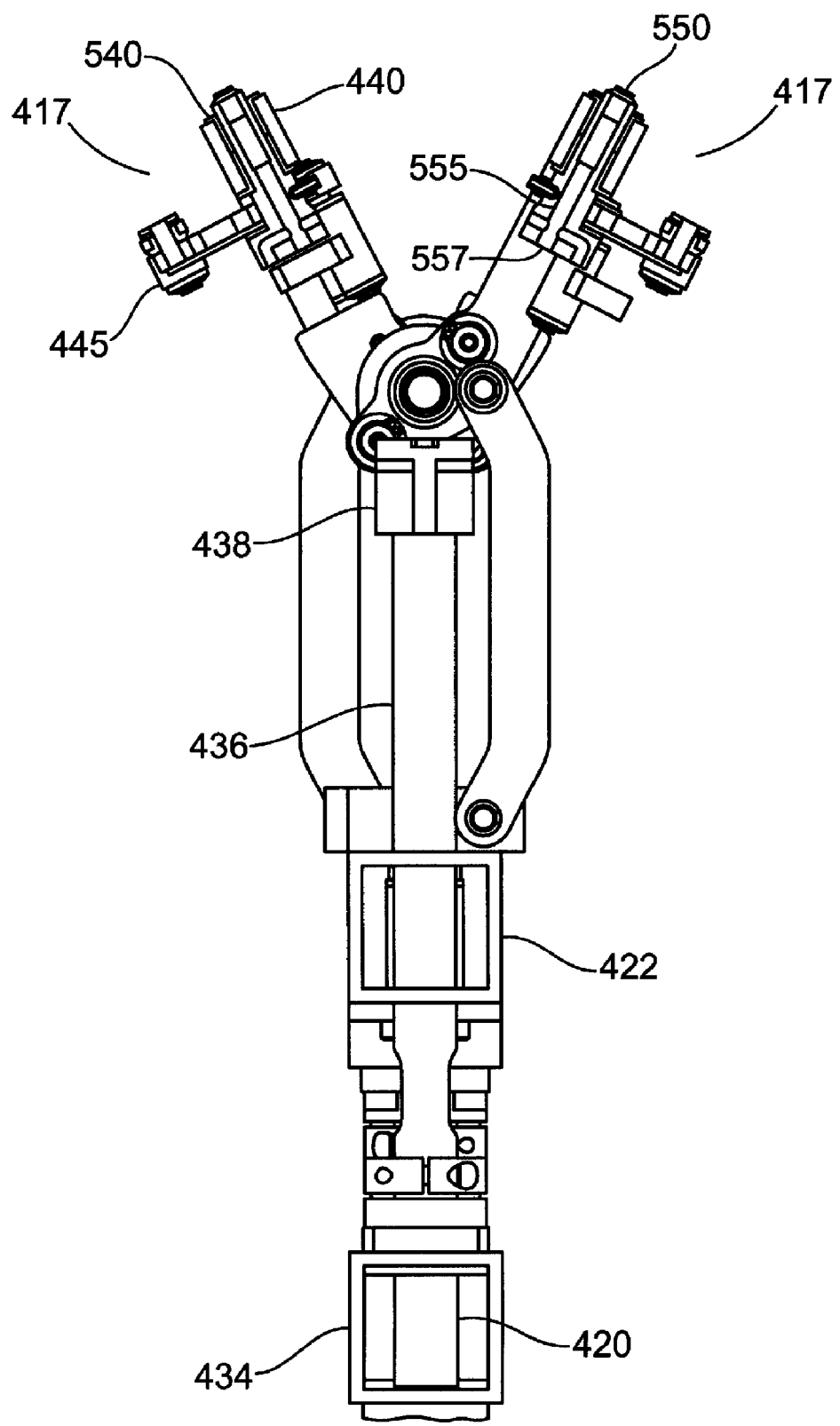
FIG. 5 is a side view of a portion of the test frame shown in FIG. 4.

FIG. 5 shows a side view of a portion of the test frame shown in FIG. 4 where the same reference numbers refer to the same structures. In FIG. 5, the torsion assembly 417 is shown in a sectional view. For purposes of clarity, the sample holder and bend tool assembly are not shown in FIG. 5. FIG. 5 also illustrates another example of the scissors type of text fixture that may be used in the simulation system. In FIG. 5, bearing 540 enables rotation of the torsion assembly 417 while the torsion assembly is supported by torsion assembly support 440. Torsion assembly 417 includes a port 557 configured to accept a variety of sample holder grips that the user may employ depending of the type of sample being tested. The port 557 is in fluid communication with a torsion assembly flow plenum 555 that provides fluid flow to the sample during testing. A loading port 550 may be opened to load the sample into the sample holder and purge air in the flow loop.

For the purposes of clarity, FIG. 4 does not show a fluid path subsystem such as the one shown in FIG. 1 but it should be understood that the embodiments shown in FIG. 4 preferably includes a fluid path subsystem. FIG. 4 does not show, again for the purposes of clarity, the controller subsystem that operates the extensor actuator 431, the scissors actuator 421, the torsion actuator 441, and the pulsatile flow pump of the fluid path subsystem, and collects sensor information on the state of the simulation system. It should be understood that the embodiments shown in FIG. 4 includes a controller subsystem much like the one described above in FIG. 1. The test fixture 402 shown in FIG. 4 has a different mechanical linkage than the fixture shown in FIG. 1 but text fixture 402 is a MIMO linkage such that the positions of both the extensor actuator 431 and scissors actuator 421 are used to calculate the sample axial strain and the sample bend angle. The controller operates the extensor actuator 431 and scissors actuator 421 in coordinated manner, based in part on a geometric model of the test fixture 402, to produce the user-desired sample axial strain and sample bend angle. In FIG. 4, the extensor actuator, scissors actuator, and torsion actuator are most preferably moving magnet linear motors but it should be understood that embodiments are not limited to moving magnet linear motors. For example and without being limiting, pneumatic actuators, hydraulic actuators, rotary electric motors may be used to generate the mechanical displacements that operate the test frame. Furthermore, combinations of different types of actuators may be used depending on the specific application of the simulation system.

The user may select a variety of torsion assembly grips and sample holders appropriate for the sample being tested. The sample holder and sample, however, couples the torsion assemblies holding each end of the sample holder. The coupling of the torsion assemblies may change the resonance properties of the test frame and may require tuning of the controller parameters that are beyond the capabilities of the user. Furthermore, a resonance near a user-desired test frequency may require a more complex controller that can account for the rapidly changing dynamic properties of the system near a resonance. For example, in a typical fatigue test, the user may wish to operate the simulation system at a high frequency to reduce the time required to complete a target number of cycles in the fatigue test. A resonance near the desired test frequency may force the user to conduct the fatigue test at a lower frequency to avoid the effects of the resonance thereby lengthening the duration of the fatigue test.

In a preferred embodiment, the extensor actuator and the scissors actuator are configured to push and pull against an additional load in parallel to operating the test fixture. The additional load acts to stiffen the system and move the natural resonance characteristics of the simulation system to a higher frequency thereby enabling fatigue testing at higher frequencies. The additional load frequently eliminates the need for controller tuning by the user as the stiffness of the additional load typically is much greater, usually at least ten times greater, than the stiffness of the various sample holder—sample combinations employed by the user.

Referring to FIG. 4, scissors crossbar 422 supports two scissors spring assemblies arranged symmetrically around support rod 420 to reduce bending stresses on the support rod 420 from an unbalanced configuration. The scissors spring assemblies include a spring support rod 470. Each spring support rod 470 supports an upper spring 473 and a lower spring 477. One end of the upper spring and one end of the lower spring are attached to the spring support rod 470. The other end of the upper spring and the other end of the lower spring are attached to a spring anchor 475. The spring anchor 475 is fixed to a frame housing 474 and provides a common mechanical reference. As the scissors crossbar 422 in displaced downward in the orientation of FIG. 4, each upper spring 473 is compressed and each lower spring 477 is stretched. Conversely, as the scissors crossbar 422 is displaced upward, each upper spring 473 is stretched and each lower spring 477 is compressed. The stretching and compression of the springs may require a more powerful actuator that can generate the greater force needed to operate the test fixture and work against the additional load. Alternatively, the user may have to reduce the number of samples tested simultaneously in order to accommodate the additional load. Selection of the springs may be based on factors that include, without being limiting, a required extension/compression of the springs, a desired axial stiffness, and a fatigue rating of the springs.

In FIG. 4, the extensor actuator 431 works against an additional load located on bypass rods 432. The bypass rods 432 are configured symmetrically about a shaft axis of the extensor actuator to reduce bending stresses arising from an unbalanced configuration. In FIG. 4, one end of an upper load spring 483 and one end of a lower load spring 487 are attached to bypass rod 432. The other end of upper load spring 483 and the other end of lower load spring 438 are attached to spring anchor 485. Spring anchor 485 is fixed to the frame housing 484 and anchors the upper load spring 483 and the lower load spring 487 to a common reference.

Figure 6:
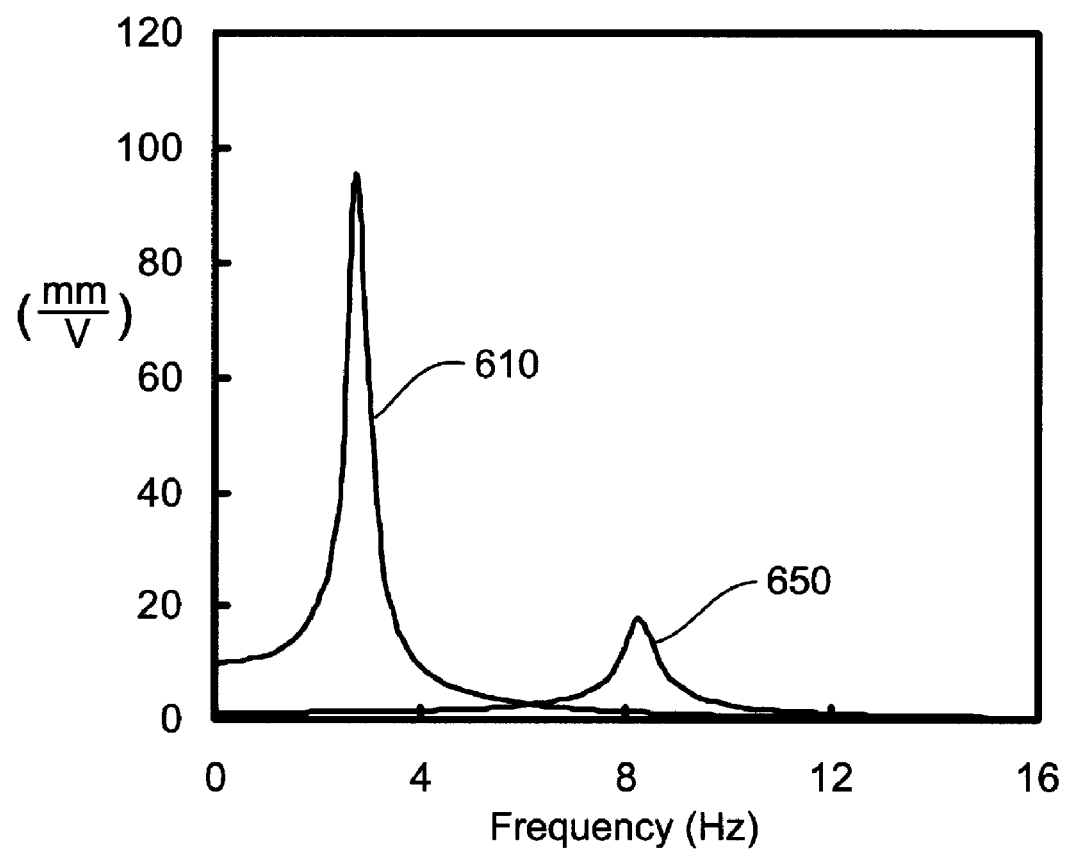
FIG. 6 illustrates a resonant characteristic of the system shown in FIG. 4.

FIG. 6 shows a resonant characteristic of the test frame shown in FIG. 4. In FIG. 6, an output, in units of mm displacement per volt input, of the scissors actuator is shown as a function of frequency without feedback control. Reference 610 illustrates the behavior of the scissors actuator without an artificial load and reference 650 illustrates the behavior of the scissors actuator with an artificial load. Reference 610 exhibits a resonance peak at around 2.8 Hz with an output gain of about 100 that would make controlling the system difficult because small changes in the input voltage creates a large displacement. Operation of the system without the artificial load may be limited to less than about 2 Hz because of the 2.8 Hz resonance. Addition of the artificial load acts to stiffen the system and move the resonance to a higher frequency as shown by reference 650 where the resonance frequency is around 8.3 Hz. The additional support bearings and structures supporting the artificial load act to dampen the resonance to a gain that allows the controller to operate around the resonant frequency. The artificial load sufficiently modifies the resonant characteristic of the actuator such that the simulation system is capable of operating at high frequencies of about 4-10 Hz over a full travel range of the actuators and may operate at higher frequencies of about 12-30 Hz over a restricted range of actuator motions.

Although FIG. 4 shows a spring as the artificial load, other embodiments may include other types or combinations of structures as the artificial load. For example, a damper may be combined with a spring to control the magnitude of the resonant peak. In another example, the artificial load may be an actuator operated by the controller to provide the desired resonant behavior modifications for the system.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed:

1. A high frequency multi-axis simulation system comprising:
   a test fixture having:
      a first linkage, the first linkage comprising first and second lever arms driven by a first actuator, the first linkage acting on a sample holder to bend the sample holder by moving first and second ends of the sample holder when driven by the first actuator, and;
      a second linkage, the second linkage comprising a bend tool driven by a second actuator, the second linkage acting on the sample holder to axially strain the sample holder and bend the sample holder by pressing on the sample when driven by the second actuator;
   a controller configured to operate the first and second actuators according to a user-specified first simulation profile and second simulation profile;
   a first artificial load driven by the first actuator; and
   a second artificial load driven by the second actuator; the first and second artificial loads increasing a resonant frequency of the simulation system;
   wherein the first and second artificial loads dominate a stiffness of the text fixture relative to a stiffness of the sample holder.

2. The system of claim 1 wherein
the test fixture further comprises:
> a first torsion assembly coupled to the first lever arm, and a second torsion assembly coupled to the second lever arm,
>> the first and second torsion assemblies driven by a third actuator to apply torque to the respective first and second ends of the sample holder; and
> the controller is further configured to operate the third actuator according to a user-specified third simulation profile.

3. The system of claim 2 wherein
> torque imparted to the sample by the first and second torsion assemblies is substantially independent of the bending and axial strain imparted to the sample by the first and second linkages, and
> the third actuator is operated simultaneously by the controller independently of the first and second actuators.

4. The system of claim 1 further comprising a flow path providing a fluid flow through the sample holder.

5. The system of claim 4 wherein
> the flow path includes a pump providing pulsatile flow through the sample holder, the pulsatile flow applying hoop strain to the sample, and
> the controller is further configured to operate the pump to control the hoop strain according to a user-specified fourth stimulation profile.

6. The system of claim 1 wherein the first artificial load is a spring.

7. The system of claim 6 wherein the first artificial load further comprises a damper.

8. The system of claim 1 wherein the resonant frequency characterizing the simulation system is greater than about 5 Hz.

9. The system of claim 1 wherein the resonant frequency characterizing the simulation system is greater than about 8 Hz.

10. The system of claim 6 wherein the spring is characterized by a stiffness having a value that is at least ten times greater than a stiffness value characterizing the sample.

11. The system of claim 1 wherein the user-specified first simulation profile is characterized by a profile frequency, the profile frequency in a frequency range of 4-10 Hz.

12. The system of claim 1 wherein the user-specified first simulation profile is characterized by a profile frequency, the profile frequency in a frequency range of 12-30 Hz.

13. The system of claim 1 wherein the first artificial load is an actuator.

14. A method of operating a high-frequency multi-axis simulation system comprising a test fixture having a first linkage comprising first and second lever arms, a second linkage comprising a bend tool, and a sample holder, the method comprising:
> driving a first artificial load and the first linkage with a first actuator to bend the sample holder by moving first and second ends of the sample holder,
> driving a second artificial load and the second linkage with a second actuator to axially strain the sample holder and bend the sample holder by pressing on the sample holder, and
> operating the first and second actuators according to a user-specified first simulation profile and second simulation profile;
> wherein
> the first and second artificial loads increase a resonant frequency of the simulation system, and
> the first and second artificial loads dominate the stiffness of the text fixture relative to a stiffness of the sample holder.

* * * * *